United States Patent [19]

Guest et al.

[11] 4,282,373
[45] Aug. 4, 1981

[54] PROCESS FOR PREPARATION OF THIOPHENES

[75] Inventors: Angela W. Guest, Little Bookham; Andrew W. Taylor, Dorking; Robert Ramage, Altrincham, all of England

[73] Assignee: Beecham Group Limited, England

[21] Appl. No.: 36,407

[22] Filed: May 7, 1979

Related U.S. Application Data

[62] Division of Ser. No. 926,727, Jul. 21, 1978, Pat. No. 4,252,976.

[30] Foreign Application Priority Data

Jul. 23, 1977 [GB] United Kingdom ............... 31008/77

[51] Int. Cl.$^3$ .......................................... C07C 69/602
[52] U.S. Cl. ................................. 560/181; 260/239.1; 260/343.3 R; 260/343.5; 260/456 P; 260/456 R; 260/465.4; 544/28; 549/74; 549/78; 549/79; 560/146; 560/184; 560/192; 560/219; 562/568; 562/571; 562/586; 562/598
[58] Field of Search ............... 560/219, 184, 192, 146, 560/181; 562/598, 586, 568, 571; 260/456 P, 456 R, 465.4, 343.3 R

[56] References Cited

U.S. PATENT DOCUMENTS

| | | | |
|---|---|---|---|
| 2,093,519 | 9/1937 | Hamann | 260/465.4 |
| 2,183,929 | 12/1939 | Bowles et al. | 544/302 |
| 2,381,882 | 8/1945 | Cupery | 260/465.4 X |
| 2,540,071 | 1/1951 | Croxall et al. | 560/219 |
| 3,360,527 | 12/1967 | Naito et al. | 260/306.7 |
| 3,801,608 | 4/1974 | Henrick | 560/192 X |

OTHER PUBLICATIONS

Stotter et al., Chem. Abst. vol. 78, Abst. No. 15946x (1973).
Beilstein's Handbuch der Organische Chemie, 4th Ed. vol. 2, Mainwerke, pp. 806-807 (System No. 180), Verlag von Julius Springer, Berlin, Germany (1920).
Beilstein's Handbuch der Organische Chemie, 4th Ed. vol. 2, Zweiter Teil, pp. 1998 to 2003 (System No. 180), Springer Verlag, Berlin, Germany 1961.
Shusherina et al., Chemical Abstracts, vol. 58, col. 9011.
Shusherina et al., English Translation of Doklady Akademii Nauk SSSR, vol. 146, No. 5, pp. 1113 to 1116 (1962), pp. 912 to 1915 of English Version.
Cavalieri, Chemical Reviews, vol. 41, pp. 525 to 526 and 573 to 577 (1947).
Houben-Weyl, Teil 4, Sauerstoff-Verbindungen I, pp. 436 to 438, Georg Thieme Verlag, Stuttgart, Germany (1966).
Chemical Abstracts Seventh Collective Index, vols. 56-65 (1962-1966), Subjects So-Til, pp. 21,165S to 21,167S, American Chemical Society, Columbus, Ohio, copyrighted 1970.
Pirkle et al., J. Am. Chem. Soc. vol. 91, pp. 1179 to 1186 (1969).
Grabowski et al., Tetrahedron, vol. 25, pp. 4315 to 4330 (1969).
Verny et al., Bull. Soc. Chim. France 1968, pp. 2585 to 2590.

Primary Examiner—John D. Randolph
Attorney, Agent, or Firm—Jacobs & Jacobs

[57] ABSTRACT

Compounds of the formula (II):

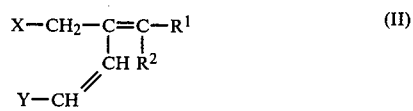

(II)

wherein X is halogen, hydroxyl or functionalized hydroxyl; Y is halogen, hydroxyl or alkoxy; $R^1$ is a carboxylic acid group and ester thereof and amide derivative thereof or cyano; and $R^2$ is hydrogen, a hydrocarbon, a heterocycle, a carboxylic acid group, a carboxylic acid ester, a carboxylic acid amide derivative, acyl, cyano, isocyano or an optionally substituted imine of the formula —CH=NZ or —N=CH$_2$ wherein Z is hydrogen, alkyl, aryl, sulphonyl, —SR$^a$, sulphoxide —SR$^a$, or sulphonate —SR$^a$ wherein R$^a$ is alkyl of 1 to 6 carbon atoms or aryl, are useful as intermediates for the ultimate production of penicillins or cephalosporins.

8 Claims, No Drawings

PROCESS FOR PREPARATION OF THIOPHENES

This is a division of Ser. No. 926,727, filed July 21, 1978, now U.S. Pat. No. 4,252,976, granted Feb. 24, 1981.

This invention relates to a chemical process for the preparation of 3-substituted thiophenes, which are useful as intermediates in the production of penicillins and cephalosporins.

A number of important penicillins and cephalosporins having a 3-thienyl group in the side-chain are well known. For example our British Pat. No: 1,004,670 describes the penicillin 'ticarcillin', viz α-carboxy-3-thienyl-methyl-penicillin, whilst esters of that compound are disclosed in our British Pat. Nos. 1,125,557 and 1,133,886. The 6α-methoxy substituted derivative of ticarcillin in disclosed in W. German Offenlegungsschrift No. 2,600,866.

α-Carboxy-3-thienylmethylcephalosporin is disclosed as an antibacterial agent in U.K. Pat. No. 1,193,302.

The most widely used method of preparation of this type of penicillin and cephalosporin is the process disclosed in British Pat. No. 1,125,557 wherein the penicillins are prepared from a 3-thienylmalonic ester itself synthesised from 3-thienylacetonitrile. The 3-thienylacetonitrile was prepared from 3-methylthiophene by the method of Campaigne et al (J.Amer.-Chem.Soc. 1948, 70, 1553) which involves reaction with N-bromo-succinimide and treatment of the resulting 3-bromomethylthiophene with sodium cyanide. However, this bromination gives the desired bromoderivative in low yield and the 3-methylthiophene starting material is unduly expensive, with the result that the final penicillin or cephalosporin is considerably more expensive than other penicillin and cephalosporin derivatives.

We have now devised a process for the preparation of 3-substituted thiophenes which involves cyclisation of a novel intermediate to form the thiophene moiety. The process is applicable to a wide variety of 3-substituents.

Accordingly the present invention provides a process for the preparation of a thiophene of formula (I):

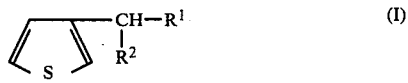

wherein $R^1$ represents a carboxylic acid group or an ester or amide derivative thereof or a nitrile (—CN) group; and $R^2$ represents hydrogen, a hydrocarbon or heterocyclic group, a carboxylic acid group or an ester or amide derivative thereof, or an acyl, nitrile, isonitrile (—NC) or optionally substituted imine group of formula —CH=NZ or —N=CHZ (where Z represents hydrogen, alkyl or aryl), or a sulphonyl, —$SR^a$, sulphoxide —$SO_2.R^a$ or sulphonate —$SO.OR^a$ group wherein $R^a$ represents $C_{1-6}$ alkyl, or aryl, which process comprises treating a compound of formula (II):

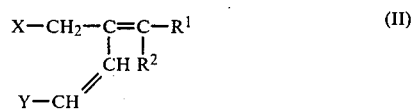

wherein $R^1$ and $R^2$ are as defined with respect to formula (I) above; X represents a halogen atom, a hydroxyl group or a functionalised hydroxyl group; and Y represents a halogen atom or a hydroxyl or alkoxy group; with a source of nucleophilic sulphur under basic conditions.

This cyclisation process may be carried out in a wide range of solvents subject to the solubility of the source of nucleophilic sulphur. It is often convenient to use a polar solvent, preferably a water-miscible solvent such as, for example, tetrahydrofuran, acetone, dimethylformamide, dimethylsulphoxide, hexamethylphosphoramide, acetonitrile, dimethoxyethane, dioxan, or an alcohol such as methanol, ethanol, propanol, butanol, in particular ethanol. Preferred solvents include tetrahydrofuran and acetone. An organic solvent such as methylene dichloride may also be employed. The reaction may be carried out at ambient to elevated temperature depending on the particular reagents used and the values of X, Y, $R^1$ and $R^2$. For example suitable temperatures for the process are from −20° C. to 100° C., preferably 10° to 50° C.

It is necessary to use a source of nucleophilic sulphur in the process of this invention. It is thought that the initial step in the process is nucleophilic displacement of the group Y in compound (II) by a sulphur moiety, and the ability to displace a group Y is the criterion for choosing a compound suitable for providing the source of nucleophilic sulphur for the process of this invention. Basic conditions are required for the subsequent step, which is thought likely to be formation of an intermediate of formula (III):

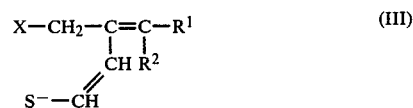

which then undergoes displacement of the group X by internal nucleophilic attack by the sulphide, $S^-$, in structure (III), an hence cyclisation to give compound (I).

Although it is usually most convenient to have the reaction under basic conditions when the source of nucleophilic sulphur is added to the compound (II), it is also possible to carry out the reaction in two steps, that is by firstly treating compound (II) with a source of nucleophilic sulphur and then subsequently completing the cyclisation reaction by addition of a base.

One suitable source of nucleophilic sulphur is for example the bisulphide ion, $HS^-$.

The bisulphide ion for the process of this invention may be provided by using a salt of this ion, preferably an alkali metal salt for example sodium bisulphide NaSH, which may be prepared, optionally in situ in the reaction, from sodium sulphide $Na_2S$ and sodium bicarbonate. An alternative, and preferred, source of the bisulphide ion comprises hydrogen sulphide and a base, which again produces $HS^-$ in situ.

This combination of reagents has the advantage that the base employed can be the same as that used for the cyclisation process itself.

Suitable bases which may be employed to provide the basic conditions for the process of this invention include inorganic bases, such as alkali metal hydroxides, preferably potassium hydroxide, and alkali metal bicarbonates preferably sodium bicarbonate and organic basis such as substituted amines for example tri($C_{1-6}$)alkylamines such as trimethylamine or triethylamine.

The bisulphide ion may also be generated in situ from sulphurated sodium borohydride, $NaBH_2S_3$.

In some cases it is possible to employ a compound for providing the source of nucleophilic sulphur, which compound is also capable of providing the basic conditions for the cyclisation step. Alkali metal bisulphides, especially sodium bisulphide, are suitable such compounds. Thus reaction of compound (II) with an alkali metal bisulphide produces an intermediate of formula (IV):

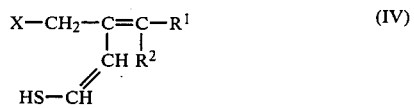
(IV)

Addition of further bisulphide (or presence of excess initially) removes a proton to give structure (III) above which then cyclises.

Another way of providing the basic conditions required for the process is to produce the intermediate ion of formula (III) directly which can then act as its own base for cyclisation. This may be achieved for example by treating compound (II) with an alkali metal sulphide, in particular sodium sulphide $Na_2S$. Because the sulphur ion in such a compound has a double negative charge, $S^{2-}$, the intermediate formed after nucleophilic attack on compound (II), is structure (III) rather than structure (IV). No further base need then be present to complete the cyclisation. This reaction is still under basic conditions by virtue of the presence of the ion (III) itself, or excess of the alkali metal sulphide; if the reaction medium became neutral or acidic, the sulphide ion in structure (III) would be protonated and the cyclisation would not proceed.

The compounds of formula (II) are novel compounds and constitute a further aspect of this invention.

In formula (II) the group X should be readily displaced by nucleophilic attack by sulphide ions. Such groups include chlorine, bromine, hydroxyl, arylsulphonyloxy such as benzenesulphonyloxy, p-toluenesulphonyloxy, or p-nitrobenzenesulphonyloxy, alkylsulphonyloxy such as methanesulphonyloxy or $C_{1-6}$ alkanoyloxy such as acetoxy, propionoxy or butyroxy.

The group Y may be, for example, chlorine, bromine, hydroxy or $C_{1-6}$ alkoxy such as methoxy, ethoxy, or propoxy. Preferably both X and Y are halogen, especially chlorine.

The radicals $R^1$ and $R^2$ in compound (II) are chosen according to the requirements of the compound (I). For the preparation of penicillin and cephalosporin derivatives the group $R^1$ should be a carboxylic acid group or a group which may be converted to a carboxylic acid group or a functional derivative thereof for acylation the amino group of the penicillin or cephalosporin nucleus. The $R^2$ group is chosen to provide the required α-substituent, or a precursor thereof, for the side chain of a penicillin or cephalosporin.

The radical $R^1$ may be an ester group —$CO_2R^3$ wherein $R^3$ is an alkyl, cycloalkyl, alkenyl, alkynyl, aryl or heterocyclic group, any of which may be substituted. Suitable such $R^3$ groups include:

(a) alkyl especially $C_{1-6}$ alkyl such as methyl, ethyl, n- and iso-propyl, n-, sec-, iso- and tert-butyl, and pentyl;

(b) substituted $C_{1-6}$ alkyl wherein the substituent is at least one of: chloro, bromo, fluoro, nitro, carbo ($C_{1-6}$ alkoxy), $C_{1-6}$ alkanoyl, $C_{1-6}$ alkoxy, cyano, $C_{1-6}$ alkylmercapto, $C_{1-6}$ alkylsulfinyl, $C_{1-6}$ alkylsulpnonyl, 1-indanyl, 2-indanyl, furyl, pyridyl, 4-imidazolyl, phthalimido, azetidino, aziridino, pyrrolidino, piperidino, morpholino, thiomorpholino, N-($C_{1-6}$ alkyl)-piperazino, pyrrolo, imidazolo, 2-imidazolino, 2,5-dimethylpyrrolidino, 1,4,5,6-tetrahydropyrimidino, 4-methylpiperidino, 2,6-dimethylpiperidino, alkylamino, dialkylamino, alkanoylamino, N-alkylanilino, or substituted N-alkylanilino wherein the substituent is chloro, bromo, $C_{1-6}$ alkyl or $C_{1-6}$ alkoxy;

(c) cycloalkyl and ($C_{1-6}$ alkyl) substituted cycloalkyl having from 3 to 7 carbon atoms in the cycloalkyl moiety;

(d) alkenyl having up to 8 carbon atoms;

(e) alkynyl having up to 8 carbon atoms;

(f) phenyl and substituted phenyl wherein the substituent is at least one of chloro, bromo, fluoro, $C_{1-6}$ alkoxy, $C_{1-6}$ alkanoyl, carbo-($C_{1-6}$) alkoxy, nitro, or di($C_{1-6}$) alkyl amino;

(g) benzyl or substituted benzyl wherein the substituent is chloro, bromo, fluoro, $C_{1-6}$ alkyl, $C_{1-6}$ alkoxy, $C_{1-6}$ alkanoyl, carbo-($C_{1-6}$)-alkoxy, nitro, or di($C_{1-6}$-alkyl) amino;

(h) a 5- or 6-membered hereocyclic group containing one or more sulphur and/or nitrogen and/or oxygen atoms in the ring optionally fused to a second 5- and 6-membered hydrocarbyl or heterocyclic ring and which may be substituted with an alkyl group having 1 to 3 carbon atoms, for example thienyl, furyl quinolyl, methyl-substituted quinolyl, phenazinyl, pyridyl, methylpyridyl, phthalidyl, indanyl.

Preferred groups for $R^3$ include $C_{1-6}$ alkyl, benzyl, phthalidyl, indanyl, phenyl, mono-, di-, and tri-($C_1$-$C_6$)alkyl substituted phenyl such as o-, m or p methylphenyl, ethylphenyl, n- or iso-propylphenyl, n-, sec-, iso- or butylphenyl.

Suitable groups $R^2$ include hydrogen, $C_{1-6}$ alkyl, such as methyl, ethyl, propyl, or butyl, benzyl, phenyl, alkylphenyl, naphthyl, a 5- or 6- membered heterocyclic group containing one or more sulphur and/or nitrogen and/or oxygen atoms in the ring and which may be substituted by an alkyl group having from 1 to 3 carbon atoms, for example thienyl, imidazolyl, thiadiazolyl, isoxazolyl, methylisoxazolyl, tetrazolyl, methyltetrazolyl, pyrimidinyl, pyridyl, pyrazinyl, pyrrolidyl, piperidyl, morpholinyl, thiazinyl, furyl, or quinolyl; a carboxylic acid group, a carboxylic ester group —$CO_2R^3$ as defined above, or a $C_{1-6}$ alkanoyl group. When both groups $R^1$ and $R^2$ are ester radicals they may together form a cyclic ester group, for example isopropylidine of formula:

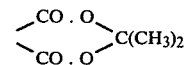

For the preparation of α-carboxy-3-thienyl penicillins and cephalosporins, $R^1$ and $R^2$ may conviently both be carboxylic acid or ester radicals. It is convenient to prepare a diester compound of formula (I), i.e. where $R^1$ and $R^2$ both represent a group —$CO_2R^3$, and then half-saponify in order to produce the compound (I) wherein one of $R^1$ and $R^2$ is a carboxylic acid group, suitable for coupling to the penicillin or cephalosporin nucleus.

Similarly for the preparation of an α-ester of an α-carboxy-3-thienyl penicillin or cephalosporin, the group $R^3$ may be chosen according to the eventual penicillin or cephalosporin required.

The compound of formula (II) above may be prepared by a process which comprises condensing a compound of formula (V):

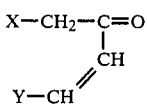  (V)

wherein X and Y are as defined above with respect to formula (II); with a compound of formula (VI):

  (VI)

wherein $R^1$ and $R^2$ are as defined above with respect to formula (I); under mild condensation conditions; and subsequently, if required, converting one group X or Y to a different such group.

The conditions used for this condensation reaction should be sufficiently mild to prevent or minimise self-condensation or other unwanted reaction of the compound (II), and the conditions and reagents employed for the reaction depend on the nature of the groups $R^1$ and $R^2$. In general, the more electron-withdrawing are the groups $R^1$ and $R^2$ then the more activated is the methylene group in compound (VI) and milder conditions may be employed.

When both the groups $R^1$ and $R^2$ are selected from a carboxylic acid group, a carboxylic ester group or an activated acyl group (for example in the form of a silyl enol ether), then the condensation of compound (V) with compound (VI) may conveniently be carried out in the presence of titanium tetrachloride and an organic nitrogen-containing base containing no acidic proton, for example pyridine. Suitable solvents for such a reaction are chlorinated hydrocarbon solvents, preferably carbon tetrachloride, optionally in the presence of a co-solvent such as tetrahydrofuran, dioxan or a polar aprotic solvent. The condensation is conveniently carried out at low to ambient temperature, preferably from 0° C. to 25° C.

Many compounds of the general formula (V) are known in the literature and may be prepared by a process which comprises reacting a compound of formula (VII):

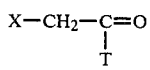  (VII)

wherein X is as defined with respect to formula (II) above and T represents halogen; with acetylene in the presence of an aluminium halide, Al U₃, wherein U represents halogen which may be the same as or different from T; to produce a compound of formula (VIII):

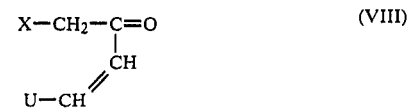

and subsequently, if required replacing the group U by a group Y and optionally converting the group X into a different such group.

This reaction may be carried out using conventional conditions known in the literature, for example as described by Naito et al, J. Antibiot (Tokyo) Ser A 20 (2), 77–86 (1967) or by Benson and Pohland, J. Org. Chem 29, 385.

The compounds of formula (I) in which one of the groups $R^1$ and $R^2$ represents a carboxylic acid function may be converted to a penicillin or cephalosporin by an method known per se, for example as described in British Pat. Nos. 1,004,670, 1,125,557, 1,133,886, 1,193,302, W. German OLS No. 2,600,866.

The following Examples illustrate this invention.

EXAMPLE 1

Preparation of 1,4-dichlorobut-3-en-2-one

Aluminium chloride (39.9 g, 0.3 mol) in carbon tetrachloride (150 ml) was treated with chloroacetylchloride (22.3 ml, 0.3 mol) while acetylene was passed through the reaction mixture. Acetylene addition was continued with stirring for 3 hours. Water was added to the reaction mixture, which was extracted with ether. The combined ether extracts were washed with saturated brine, N sodium bicarbonate solution, saturated brine, dried and evaporated to give the crude title compound (34.1 g, 82%) as a mixture of cis and trans isomers. Cis isomer δ (CDCl₃) 4.32 (2H, s, CH₂), 6.66 (1H, d, 8 Hz, —CH=), 6.88 (1H, d, J 8 Hz, —CH=), trans isomer δ (CDCl₃) 4.22 (2H, s, CH₂), 6.82 (1H, d, J 14 Hz, CH=), 7.52 (1H, d, J 14 Hz, CH=). $\nu_{max}$ (film) 1580, 1690 cm⁻¹.

EXAMPLE 2

Preparation of trans 1,4-dichlorobut-3-en-2-one

Aluminium chloride (79.8 g, 0.6 mol) in methylene dichloride (300 ml) was treated with stirring with chloroacetyl chloride (44.6 ml, 0.56 mol). Acetylene (ca 1.2 mol) was passed throught the reaction mixture with stirring for three hours at a flow rate of 150 ml/min. The reaction solution was slowly treated with ice-water (200 ml), and the mixture extracted with methylene dichloride (200 ml, 2×100 ml). The combined extracts are washed with brine (2×50 ml) and saturated sodium bicarbonate (50 ml), dried (Na₂SO₄) and evaporated to give the title product in 74% yield, b.p. 71°–74°/10 mm. δ (CDCl₃) 4.22 (2H, s, CH₂), 6.82 (1H, d, J 14 Hz, CH=), 7.52 (1H, d, J 14 Hz, CH=); $\nu_{max}$ (film) 1580, 1690 cm⁻¹.

EXAMPLE 3

Preparation of cis 1,4-dichlorobut-3-en-2-one

The procedure described in Example 2 was repeated, but with a shorter reaction time (ninety minutes) to give a 50:50 mixture of cis and trans isomers. Chromatography (silica gel; 10% ethyl acetate in 60–80 petrol ether afforded the slower moving cis isomer (29% yield). δ (CDCl₃) 4.35 (2H, s, CH₂), 6.67 (1H, d, J 8 Hz, CH=), 6,90 (1H, d, J 8 Hz, CH=). $\nu_{max}$ (ethanol) 239 nm ($\epsilon_m = 8,450$). $\nu_{max}$(film) 1595, 1690, 1710 cm$^{-1}$. Found: M+ 138. C$_4$H$_4$Cl$_2$O requires M, 138.

EXAMPLE 4

Preparation of 4-trans ethyl-2-ethoxycarbonyl-5-chloro-3-chloromethyl penta-2,4-dienoate Titanium tetrachloride (10 ml., 0.1 mol) in CCl$_4$ (10 ml) was added to tetrahydrofuran (25 ml) at 0°. A premix of trans 1,4-dichlorobut-3-en-2-one (5.6 g, 0.04 mol) and diethyl malonate (6.45 g., 0.04 mol) was added in tetrahydrofuran (20 ml). Over 20 minutes, pyridine (13.0 ml., 0.16 mol) in tetrahydrofuran (10 ml) was added. The reaction mixture was stirred for three hours at room temperature, diluted with water (100 ml) and extracted with MDC (50 ml., 2×25ml). The combined extracts were washed with brine (2×20 ml), N sodium bicarbonate solution (20 ml), dried (Na$_2$SO$_4$) and evaporated to give the title product (61% yield). δ (CDCl$_3$) 1.37 (6H, t, J 7 Hz, CH$_3$), 4.39 (4H, q, J 7 Hz, OCH$_2$), 4.62 (2H, s, CH$_2$), 7.12 (2H, s, CH=CH). $\nu_{max}$ (film) 1610, 1720 cm$^{-1}$. C$_{11}$H$_{14}$O$_4$Cl$_2$ requires M, 280.0269. Found: M+, 280.0256.

EXAMPLE 5

Preparation of 4-cis ethyl-2-ethoxycarbonyl-5-chloro-3-chloromethyl penta-2,4-dienoate Cis 1,4-Dichlorobut-3-en-2-one was condensed with diethyl malonate under the conditions described in Example 4, to give the title product (67% yield). δ (CDCl$_3$) 1.28 (3H, t, J 7 Hz, CH$_3$), 1.33 (3H, t, J 7 Hz, CH$_3$), 4.26 (2H, q, J 7 Hz, OCH$_2$), 4.33 (2H, q, J 7 Hz, OCH$_2$), 4.67 (2H, s, CH$_2$), 6.35 (1H, d, J 8 Hz, CH=), 6.70 (1H, d, J 8 Hz, CH=). $\nu_{max}$ (ethanol) 269 nm ($\epsilon_m = 6,000$). $\nu_{max}$ (film) 1610, 1720 cm$^{-1}$.

EXAMPLE 6

Preparation of 4-trans methyl-2-methoxycarbonyl-5-chloro-3-chloromethyl penta-2,4-dienoate Titanium tetrachloride (10 ml., 0.1 mol) in carbon tetrachloride (25 ml) was added to tetrahydrofuran (THF) (250 ml) at 0° C. A premix of trans-1,4-dichlorobut-3-en-2-one (5.6 g., 0.04 mol) and diethylmalonate (4.2 ml., 0.037 mol) in THF (20 ml) was added. Pyridine (13.0 g., 0.16 mol) in THF (80 ml) was added over 20 mins. The reaction mixture was stirred at room temperature for 16 hours, diluted with water, and extracted with ether. The ether extracts were washed with brine, sodium bicarbonate solution, and brine. Drying and evaporation gave the title compound (7.72 g., 77%). Recrystallisation from ether:petrol gave large prisms, m.p. 56°, $\nu_{max}$ (film) 1730, 1610 cm$^{-1}$, δ (CDCL$_3$) 3.85 (6H, s, 2×CH$_3$), 4.60 (2H, s, CH$_2$), 7.03 (2H, s, CH=CH). Found: C, 42.9; H, 4.0; Cl, 28.0% C$_9$H$_{10}$O$_4$Cl$_2$ requires C, 42.7; H, 4.0; Cl, 28.0%.

EXAMPLE 7

Preparation of 4-trans methyl-2-methoxycarbonyl-5-chloromethyl penta-2,4-dienoate Titanium tetrachloride (0.5 ml, 5.0 mol) in carbon tetrachloride (1.5 ml) was added to THF (10 ml) at 0° C. A premix of trans-1,4-dichlorobut-3-en-2-one (0.28 g., 2.0 mol) and diethyl malonate (0.22 ml., 2.0 mol) in THF (2 ml) was added. Over 5 minutes, pyridine (0.32 ml., 4.0 mol) in THF (4 ml) was added. Calcium carbonate (0.4 g., 4.0 mol) was added and the reaction mixture stirred at room temperature for 3 hours, diluted with water and extracted with ether. The ether extracts were washed with brine, sodium bicarbonate solution, brine; dried, treated with charcoal and evaporated to give the title compound in 69% yield, purified as in Example 6 (Spectroscopic data as in Example 6).

EXAMPLE 8

Preparation of 4-trans-benzyl-2-benzyloxycarbonyl-5-chloro-3-chloromethyl penta-2,4-dienoate Trans-1,4-dichlorobut-3-en-2-one (2.8 g., 20.0 mmol) and dibenzyl malonate (5.7 g., 20.0 mmol) were condensed as in Example 6 using the TiCl$_4$/pyridine method, thus affording the title compound in 46% yield. Recrystallization from ethanol gave prisms, m.p. 45°–6°, $\nu_{max}$ (CH$_2$Cl$_2$) 1730, 1610 cm$^{-1}$, δ (CDCl$_3$), 4.50 (2H, s, ClCH$_2$), 5.24 (4H, s, 2×PhCH$_2$—), 7.00 (2H, s, CH=CH), 7.36 (10H, s, arylprotons), $\lambda_{max}$ (EtOH) 277 nm (ε 22,100).

EXAMPLE 9

Preparation of 4-cis 2-carboxy-5-chloro-3-chloromethyl penta-2,4-dienoic acid Titanium tetrachloride (2.5 ml., 25 mmol) in carbon tetrachloride (7.5 ml) was added to THF (60 ml) at 0° C. Malonic acid (1.0 g., 10 mmol) and trans 1,4-dichlorobut-3-en-2-one (1.4 g., 10 mmol) in THF (10 ml) was added. Pyridine (3.3 ml., 40 mmol) in THF (10 ml) was added dropwise over fifteen minutes at 0° C. The reaction mixture was stirred at room temperature for three hours, diluted with water (50 ml) and extracted with ether (50 ml., 2×25 ml). The extracts were washed with brine, N sodium bicarbonate solution, brine, dried (Na$_2$SO$_4$) and evaporated to give the title product (0.35 g., 12%). δ (CDCl$_3$) 5.00 (2H, s, CH$_2$), 6.91 (1H, d, J 5 Hz, CH=), 8.01 (1H, d, J 5 Hz, CH=), 9.68 (2H, s, —OH). $\nu_{max}$ (CHCl$_3$) 1720 cm$^{-1}$.

EXAMPLE 10

Preparation of 4-trans-ethyl-2-cyano-5-chloro-3-chloromethyl penta-2,4-dienoate Titanium tetrachloride (0.25 ml, 2.5 mmol) in CCl$_4$ (1.5 ml) was added to THF (10 ml) at 0° C. Trans-1,4-dichlorobut-3-en-2-one (0.28 g, 2.0 mmol) and ethyl cyanoacetate (0.21 g, 1.9 mmol) in THF (2 ml) were added. Pyridine (0.32 ml, 4.0 mmol) in THF (5 ml) was added over 5 minutes, and the mixture stirred for eighteen hours at room temperature. Work up as in example 6 gave the title compound (0.04 g, 8%). The E:Z isomeric mixture possessed δ (CDCl$_3$) 1.37 (3H, t, J 7 Hz, CH$_3$), 4.39 (2H, q, J 7 Hz, CH$_3$), 4.60 (2H, s, CH$_2$), 7.30 (2H, complex, CH=CH); 1.42 (3H, t, J Hz, CH$_3$), 4.43 (2H, q, J 7 Hz, CH$_2$), 4.93 (2H, s, CH$_2$), 7.30 (2H, complex, CH=CH).

EXAMPLE 11

Preparation of methyl-5-chloro-3-chloromethyl penta-2,4-dienoate (cis/trans mixture)

Cis-1,4-dichlorobut-3-en-2-one (0.28 g, 2.0 mmol) in toluene (5 ml) was heated at 90° C. with carbomethoxymethylene triphenylphosphorane (0.66 g, 2.0 mmol) for 15 hours. Water was added, and extracted with ether. Drying, evaporation and chromatography on silica gave the title compound as a mixture of $\Delta_{4,5}$ cis and trans-isomers (0.05 g, 13%), $\nu_{max}$(film) 1720, 1625 cm$^{-1}$; δ (CDCl$_3$) (cis-isomer) 3.60 (3H, s, —CH$_3$), 4.55 (2H, s, —CH$_2$—), 6.23 (1H, s, CHCO$_2$—), 6.37 (1H, d, J 8 Hz, CH=), 7.27 (1H, d, J 8 Hz, CH=); (trans-isomer) 3.60 (3H, s, —CH$_3$), 4.40 (2H, s, —CH$_2$—), 6.03 (1H, s, CHCO$_2$—), 6.85 (1H, d, J 14 Hz, CH=), 7.95 (1H, d, J 14 Hz, CH=).

EXAMPLE 12

Preparation of 4-trans methyl-5-chloro-3-chloromethyl-penta-2,4-dienoate

Trans 1,4-Dichlorobut-3-en-2-one (0.56 g, 4.0 mmol) in toluene (10 ml) was stirred with methoxycarbonyl-methylenetriphenyl phosphorane (1.32 g, 4.0 mmol) at 90° C. for sixteen hours. Water (50 ml) was added and the mixture extracted with ether (50 ml, 2×25 ml). The extracts were dried (Na$_2$SO$_4$) and evaporated to give the title compound (0.11 g, 14%), spectral details as in Example 11.

EXAMPLE 13

Preparation of diethylthien-3-yl malonate

Potassium hydroxide (0.14 g, 2.0 mmol) in ethanol (50 ml) was saturated with hydrogen sulphide at 0° for one hour. To this was added 4-trans ethyl-2-ethoxycarbonyl-5-chloro-3-chloromethylpenta-2,4-dienoate (0.62 g, 2.45 mmol), and addition of hydrogen sulphide was continued for one hour at room temperature. The reaction mixture was stirred for a further four hours. Potassium hydroxide (0.20 g, 2.8 mmol) was added and hydrogen sulphide passed for thirty minutes. The reaction mixture was stirred at room temperature for sixteen hours, diluted with water (50 ml) and extracted with ether (3×50 ml). The extracts were washed with saturated brine, N sodium bicarbonate solution, saturated brine, dried (Na$_2$SO$_4$) and evaporated to give the title compound (78% yield) purified by distillation, b.p. 119°–127°/0.5 mm. δ (CDCl$_3$) 1.27 (6H, t, J 7 Hz, CH$_3$), 4.20 (4H, q, J 7 Hz, OCH$_2$), 4.75 (1H, s, CH), 7.20–7.43 (3H, m, thienyl protons), $\nu_{max}$(film) 1730 cm$^{-1}$, $\lambda_{max}$ (ethanol) 234 nm. C$_{11}$H$_{14}$O$_4$S requires M, 242.0649. Found M$^+$, 242.0609.

EXAMPLE 14

Preparation of diethylthien-3-yl malonate 4-trans Ethyl 2-ethoxycarbonyl-5-chloro-3-chloromethyl penta-2,4-dienoate (0.28 g, 1.0 mmol) in THF (5 ml) was treated with solid sodium sulphide nonahydrate (0.24 g, 1.0 mmol) and the mixture stirred at room temperature for sixteen hours. Ether (50 ml) was added; brine washing, drying (Na$_2$SO$_4$), charcoal and evaporation gave the title product (66% yield), spectral details as in Example 13.

EXAMPLE 15

Preparation of diethylthien-3-yl malonate

Sodium sulphide (Na$_2$S.9H$_2$O (12 g, 0.05 mol) was dissolved in water and the volume made up to 35 ml. Sodium bicarbonate (4.2 g, 0.05 mol) was added with stirring. After dissolution, methanol (30 ml) was added. After thirty minutes, sodium carbonate was filtered off, and the solids washed with methanol (15 ml). There is thus obtained a solution of sodium bisulphide (50 mmol) in aqueous methanol.

4-trans Ethyl 2-ethoxycarbonyl-5-chloro-3-chloromethyl penta-2,4-dienoate (1.4 g, 5 mmol) in methanol (50 ml) was treated at 10° C., dropwise with sodium bisulphide solution (8 ml, 5 mmol). After two hours at room temperature, a further aliquot of sodium bisulphide solution (8 ml, 5 mmol) was added and the mixture stirred overnight. The solution was concentrated (ca 5 ml) and water (50 ml) added. Ether extraction (3×50 ml), brine washing (50 ml) drying (Na$_2$SO$_4$), charcoal and evaporation gave the title product (68% yield), spectral details as in Example 13.

EXAMPLE 16

Preparation of diethylthien-3-yl malonate 4-trans Ethyl 2-ethoxycarbonyl-5-chloro-3-chloromethyl penta-2,4-dienoate (0.28 g, 1.0 mmol) in methylene dichloride (10 ml) at 0°–5° C. was treated with hydrogen sulphide for ten minutes. A solution of triethylamine (0.28 ml, 2.0 mmol) in methylene dichloride (5 ml) was added over five minutes, and the solution stirred at room temperature for forty-five minutes, diluted with methylene dichloride (25 ml), washed with brine (25 ml) dried (Na$_2$SO$_4$) and evaporated to give the title product (62% yield), spectral details as in Example 13.

EXAMPLE 17

Preparation of diethylthien-3-yl malonate 4-cis Ethyl-2-ethoxycarbonyl-5-chloro-3-chloromethyl penta-2,4-dienoate (0.84 g, 3.0 mmol) in tetrahydrofuran (15 ml) was stirred with sodium sulphide nonahydrate (0.72 g, 3.0 mmol) at room temperature for sixteen hours. The reaction mixture was diluted with ether, washed with brine, dried (Na$_2$SO$_4$), treated with charcoal, filtered and evaporated to give the title product (0.18 g, 28%), spectral details as in Example 13.

EXAMPLE 18

Preparation of dimethyl thien-3-yl malonate 4-trans Methyl-2-methoxycarbonyl-5-chloro-3-chloromethyl penta-2,4-dienoate (1.25 g., 5.0 mmol.) in THF (15 ml) was stirred for 18 hours with sodium sulphide nonahydrate (1.68 g., 7.0 mmol.). The solution was diluted with ether, washed with water, dried (Na$_2$SO$_4$) and evaporated to give the reaction product, which, on filtration through coarse fluorosil (3.5 g.), gave decolorized title compound (0.61 g., 57%), b.p. 96°–98° (0.3 mm), $\nu_{max}$ (film) 1740 cm$^{-1}$, δ(CDCl$_3$), 3.77 (6H, s, 2×CH$_3$), 4.82 (1H, s, —CH), 7.11–7.48 (3H, complex, thienyl protons). C$_9$H$_{10}$O$_4$S requires M, 214. Found: M$^+$, 214.

EXAMPLE 19

Preparation of dibenzyl thien-3-yl malonate 4-trans Benzyl-2-benzyloxycarbonyl-5-chloro-3-chloromethyl penta-2,4-dienoate was treated with sodium sulphide as in example 18 thus affording the title compound in 71% yield. Recrystallization from toluene petrol gave prisms, m.p. 49°–50°, $\nu_{max}$ (CH$_2$Cl$_2$) 1740 cm$^{-1}$, δ(CDCl$_3$) 4.88 (1H, s, CH), 5.18 (4H, s, 2CH$_2$), 7.33 (13H, complex, aryl and thienyl protons).

EXAMPLE 20

Preparation of ethyl thien-3'-yl cyanoacetate

4-Trans ethyl-2-cyano-5-chloro-3-chloromethyl penta-2,4-dienoate was treated with sodium sulphide nonahydrate as in example 18 thus affording the title compound in 30% yield, $\nu_{max}$ (CH$_2$Cl$_2$) 1720 cm$^{-1}$, $\delta$(CDCl$_3$) 1.27 (3H, t, J 7 Hz, CH$_2$), 4.80 (IH, s, CH), 7.2–7.6 (3H, complex, thienyl protons).

EXAMPLE 21

Preparation of methyl thien-3-yl acetate

Potassium hydroxide (0.04 g., 0.6 mmol.) in ethanol (10 ml) at 0° was saturated with H$_2$S for 15 minutes. 4-Trans methyl-5-chloro-3-chloromethyl penta-2,4-dienoate (0.11 g., 0.56 mmol) was added, and the solution stirred with continued H$_2$S addition for 1 hour. Further potassium hydroxide (0.04 g., 0.6 mmol.) in ethanol (2 ml.) was added. The solution was stirred at room temperature for 18 hours, diluted with water and extracted with ether, which was dried and evaporated to give the title compound (0.07 g.) $\nu_{max}$ (CHCl$_3$) 1730 cm$^{-1}$, $\delta$ (CDCl$_3$) 3.71 (5H, s, —CH$_2$— and —CH$_3$), 7.0–7.6 (3H, complex, thienyl protons), $\lambda_{max}$ (EtOH) 224 ($\epsilon$4,560), 265 nm ($\epsilon$2,440). C$_7$H$_8$O$_2$S requires M, 156 Found: M+, 156.

(This compound may also be prepared using preformed sodium bisulphide in place of H$_2$S/KOH.)

EXAMPLE 22

Preparation of dimethyl thien-3-yl malonate

Potassium hydroxide (0.14 g, 2.0 mmol) in ethanol (50 ml) was saturated with hydrogen sulphide at 0° C. To this was added methyl-2-methoxycarbonyl-5-chloro-3-chloromethylpenta-2,4-dienoate (0.62 g, 2.45 mmol) and addition of hydrogen sulphide was continued for 1 hour at room temperature. The reaction mixture was stirred for a further 4 hours. Potassium hydroxide (0.20 g, 2.8 mmol) was added and hydrogen sulphide passed for 0.5 hours. The reaction mixture was stirred at room temperature for 16 hours, diluted with water and ether extracted. The extracts were washed with saturated brine, dried and evaporated to give the title compound (0.39 g, 74%), b.p. 96°–98° C./0.3 mm. $\delta$ (CDCl$_3$) 3.77 (6H, s, 2×CH$_3$), 4.82 (1H, s, CH), 7.11–7.48 (3H, m, thienyl protons), $\nu_{max}$ (film) 1740 cm$^{-1}$ C$_9$H$_{10}$O$_4$S requires M, 214. Found: M+, 214.

We claim:

1. A compound of the formula:

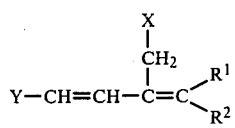

wherein

R$^1$ is

and

R$^2$ is the same or different

R$^3$ is hydrogen, alkyl of 1 to 6 carbon atoms, benzyl, phthalidyl, indanyl, phenyl or phenyl substituted with from 1 to 3 alkyl groups each of from 1 to 6 carbon atoms, Y is halo, hydroxy or alkoxy, and X is halo, hydroxy benzenesulphonyloxy, p-toluenesulphonyloxy, p-nitrobenzene-sulphonyloxy, alkylsulphonyloxy, or alkanoyloxy of 1 to 6 carbon atoms.

2. A compound according to claim 1 wherein X is chloro, bromo or hydroxy.

3. A compound according to claim 1 wherein Y is chloro, bromo, hydroxy, or alkoxy of 1 to 6 carbon atoms.

4. A compound according to claim 1 wherein X and Y are both chloro.

5. A compound according to claim 1 wherein X and Y are both halo.

6. A compound according to claim 1 wherein R$^1$ and R$^2$ is the carboxylic acid group or an ester thereof.

7. A compound according to claim 1 wherein R$^3$ is hydrogen, alkyl of 1 to 6 carbon atoms or benzyl.

8. A compound according to claim 7 wherein R$_3$ is hydrogen, methyl, ethyl or benzyl.

* * * * *